(12) United States Patent
Moudgil et al.

(10) Patent No.: US 9,763,440 B2
(45) Date of Patent: Sep. 19, 2017

(54) COLORED CLAYS FOR AGRICULTURAL AND OTHER INDUSTRIAL APPLICATIONS

(71) Applicant: University of Florida Research Foundation, Inc., Gainesville, FL (US)

(72) Inventors: Brij M. Moudgil, Gainesville, FL (US); Savino C. Musella, Lake Wales, FL (US); Edgardo Etxeberria, Auburndale, FL (US); Michael E. Rogers, Lakeland, FL (US); Craig R. Brodersen, Niantic, CT (US); Parvesh Sharma, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

(21) Appl. No.: 15/221,645

(22) Filed: Jul. 28, 2016

(65) Prior Publication Data
US 2017/0027165 A1 Feb. 2, 2017

Related U.S. Application Data

(60) Provisional application No. 62/199,020, filed on Jul. 30, 2015.

(51) Int. Cl.
*A01N 25/12* (2006.01)
*A01N 25/30* (2006.01)
*A01N 25/24* (2006.01)

(52) U.S. Cl.
CPC ............. *A01N 25/12* (2013.01); *A01N 25/24* (2013.01); *A01N 25/30* (2013.01)

(58) Field of Classification Search
None
See application file for complete search history.

(56) References Cited

U.S. PATENT DOCUMENTS 5,415,877 A * 5/1995 Winston ................. A01N 59/04
424/682
6,464,995 B1 10/2002 Sekutowski et al.
(Continued)

FOREIGN PATENT DOCUMENTS

WO    WO 2013-123176    8/2013

OTHER PUBLICATIONS

FDA colorant list ([retrieved from on-line website: http://www.fda.gov/ForIndustry/ColorAdditives/RegulatoryProcessHistoricalPerspectives/, pp. 1-10, 2003 issued, last visit Jan. 21, 2017]).*

(Continued)

*Primary Examiner* — Ernst V Arnold
*Assistant Examiner* — Kyung Sook Chang
(74) *Attorney, Agent, or Firm* — Saliwanchik, Lloyd and Eisenschenk

(57) ABSTRACT

Colored clay particles are prepared by the absorption of pigments, such as dyes, on the surface of clays. The surface of the clay can be modified with a surfactant such that a dye can be well bound to the particle's surface to avoid leaching of the dye into water. The colored clay particles can be used to deter insects, such as the Asian Citrus Psyllid (ACP), by coating a plant, such as a citrus plant, with the colored clay particles. The reflectance of the visible and ultraviolet light can be altered by the choice of dyes such that the spectrum visible to the insect deters the insect from the plant.

10 Claims, 9 Drawing Sheets

(56) References Cited

U.S. PATENT DOCUMENTS

Figure 1:
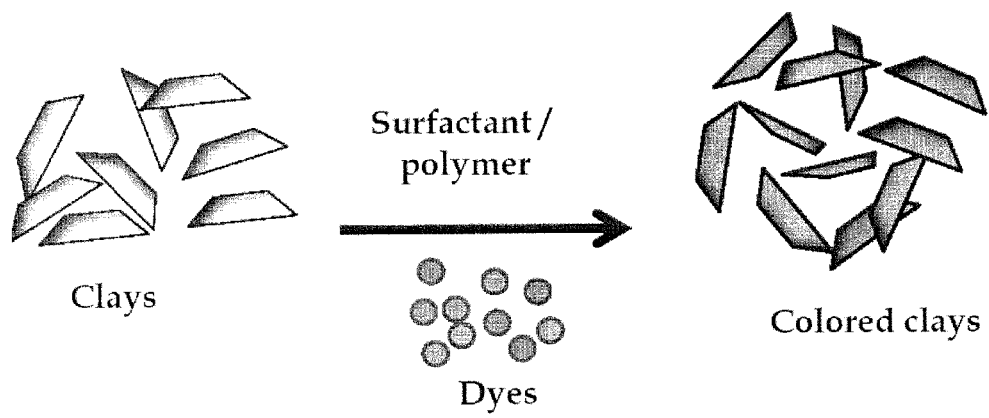

| | | | |
|---|---|---|---|
| 8,637,091 B2 | 1/2014 | Pluta et al. | |
| 2006/0252649 A1* | 11/2006 | Pluta | A01N 25/12 504/367 |
| 2009/0069386 A1* | 3/2009 | Dairiki | A01N 25/02 514/341 |
| 2015/0056259 A1 | 2/2015 | Sharma et al. | |

OTHER PUBLICATIONS

Kim, K.D., "Integrated Mangement of Asian Citrus Psyllid, *Diaphorina Citri* Kuwayama, for Protecting Young Citrus Trees from Huanglongbing," *A Disseration presented to the graduate school of the University of Florida for the degree of Philosophy*, 2013.

Sharma, P., "Optical and physical deterrent for preventing ACP vector attack on citrus," *Citrus Advanced Technology Program, Quarterly & Final Reports: Control of Citrus Greening, Canker & Emerging Diseases of Citrus*, [online, webpage, retrieved Oct. 5, 2016] from: http://research.citrusrdf.org/reports/2015/04/15/860_Optical_and_physical_deterrent_April_2015_.pdf, p. 1.

Surround WP Crop Protectant Against Insect Pests for Organic and Conventional Fruit, Vegetable and Tree Nut Production product information, New Brunswick, Canada, Oct. 2009 [online, webpage, retrieved Oct. 5, 2016] from: https://www.gnb.ca/0174/01740008-e.pdf, pp. 1-4.

Saour, G. et al. Efficacy of Kaolin particle film and selected synthetic insecticides against pistachio psyllid *Agonoscena targionii* (Homoptera: Psyllidae) infestation, *Crop Protection*, 2005, pp. 711-717, vol. 24, No. 8.

Korifi, R. et al., "CIEL a b color space predictive models for colorimetry devices—Analysis of perfume quality," *Talanta*, 2013, pp. 58-66, vol. 104.

Becerir, B., Assessment of Colour Properties of Reactive Dyed Cotton Fabrics Under Different Illuminants by Using Cielab and Hunter Systems, *Tekst Konfeksiyon*, 2010, pp. 145-154, vol. 20, No. 2.

Cottrell, T.E. et al., "Particle Film Affects Black Pecan Aphid (Homoptera: Aphididae) on Pecan," *Journal of Economic Entomology*, 2002, pp. 782-788, vol. 95, No. 4.

Daniel, C. et al. "Processed kaolin as an alternative insecticide against the European pear sucker, *Cacopsylla pyri* (L.)," *Journal of Applied Entomology*, 2005, pp. 363-367, vol. 129, No. 7.

Erler, F. et al., "Effect of Kaolin Particle Film Treatment on Winterform Oviposition of the Pear Psylla *Cacopsylla pyri*," *Phytoparasitica*, 2007, pp. 466-473, vol. 35, No. 5.

Glenn, D.M. et al., "Particle Films: A New Technology for Agriculture," *Horticultural Reviews*, 2005, pp. 1-44, vol. 31.

Hall, D.G. et al., "Effects of a Particle Film on Biology and Behavior of *Diaphorina citri* (Hemiptera: Psyllidae) and Its Infestations in Citrus," *Journal of Economic Entomology*, 2007, pp. 847-854, vol. 100, No. 3.

Jifon, J.L. et al., "Kaolin Particle Film Applications Can Increase Photosynthesis and Water Use Efficiency of 'Ruby Red' Grapefruit Leaves," *Journal of the American Society for Horticultural Science*, 2003, pp. 107-112, vol. 128, No. 1.

Liang, G. et al. "Repellency of a Kaolin Particle Film, Surround, and a Mineral Oil, Sunspray Oil, to Silverleaf Whitefly (Homoptera: Aleyrodidae) on Melon in the Laboratory," *Journal of Economic Entomology*, 2002, pp. 317-324, vol. 95, No. 2.

Showler, A.T., "Effects of Kaolin-Based Particle Film Application on Boll Weevil (Coleoptera: Curculionidae) Injury to Cotton," *Journal of Economic Entomology*, 2000, pp. 754-762, vol. 95, No. 4.

Unruh, T.R. et al., "Particle Films for Suppression of the Codling Moth (Lepidoptera: Tortricadae) in Apple and Pear Orchards," *Journal of Economic Entomology*, 2000, pp. 737-743, vol. 93, No. 3.

* cited by examiner

FD&C Red 40

D&C Violet 2

COLORED CLAYS FOR AGRICULTURAL AND OTHER INDUSTRIAL APPLICATIONS

CROSS-REFERENCE TO A RELATED APPLICATION

This application claims the benefit of U.S. Provisional Application Ser. No. 62/199,020, filed Jul. 30, 2015, the disclosure of which is hereby incorporated by reference in its entirety, including all figures, tables and drawings.

BACKGROUND OF INVENTION

Huanglongbing (HLB; syn Citrus Greening or yellow dragon) disease is one of the biggest threats to the $9.3B Florida citrus industry. Currently, the disease is widespread throughout all of the citrus growing regions in Florida, and was recently discovered in both California and Texas. This disease is caused by bacteria and is spread by Asian Citrus Psyllid (ACP) insect. As diurnal insects, *D. citri* are strongly responsive to visual host plant cues (Unruh et al. *Journal Of Economic Entomology* 2000, 93(3), 737-43, Showier et al. *Journal Of Economic Entomology* 2000, 95(4), 754-62). Recent laboratory studies report enhancement of attraction to host plant odors in the presence of visual cues, (Cottrell et al. *Journal of Economic Entomology* 2002, 95(4) 782-8. Hall et al. *Journal of Economic Entomology* 2007, 100(3), 847-54) indicating the critical role of vision in host plant location. While adult *D. citri* feed on Rutanceous host plant leaves of any age, only flush tissues support reproductive development, oviposition and nymphal growth (Liang et al. *Journal of Economic Entomology* 2002, 95(2), 317-245). Based on sticky trap collections, *D. citri* are strongly attracted to reflected yellow and green light (thought to represent leaf color) but not attracted to blue wavelengths (Hall et al., Erler et al. *Phytoparasitica* 2007, 35(5), 466-73). Similar to aphids and whiteflies, ultraviolet-reflecting materials also appear to repel psyllids (Saour et al. *Crop Protection* 2005, 24(8), 711-7, Daniel et al. *Journal of Applied Entomology* 2005, 129(7), 363-77).

Particle film technology has been reported to be an environment friendly, sustainable, and viable alternative to chemical insecticide for managing pests and diseases in agricultural crops. Hence the development of spectral reflector for spreading on the plants to modify or alter the optical cues that ACP use to identify citrus as a food source is of value. The spectral reflector must be easily spread on the plant and retained on the plant for effective repelling of the ACP.

SUMMARY OF THE INVENTION

An embodiment of the invention is directed to colored clay particles where a clay particle has one or more pigments absorbed thereon. The colored clay particle can include a cationic or anionic surfactant. The colored clay particles can be kaolin particles and the pigment can be an acidic or a basic dye. Dyes that can be used include FD&C Blue 1, FD&C Blue 2, Basic Blue 54, Bright Red, FD&C Red 40, Crystal Violet, Cert Green, Fluor Green, FD&C Yellow 5, Basic Yellow 29, or D&C Violet 2. The colored clay particles can also include an adjuvant for spreading and sticking, such as Xanthan Gum; Kollicoat (30% poly vinyl acetate dispersion in water); or Polymer adjuvant (6% sodium poly acrylate in water).

Another embodiment of the invention is directed to a method of repelling insects, where colored clay particles, as described above, are used to coat a surface, such as the surface of a plant. The colored clay particles can comprise Bright red, FD&C Red and/or FD&C Violet. The repelling colored particle coated plants can be used in conjunction with a trap that includes plant surfaces with attracting colored clay particles, such as colored clay particles comprising FD&C Yellow.

BRIEF DESCRIPTION OF DRAWINGS

FIG. 1 is a scheme for the treatment of clays with dyes via a surfactant to achieve colored clays, according to embodiments of the invention.

FIG. 2 shows photograph of colored clays where a surfactant has been employed as a surface modifier to minimize leaching of dyes from colored clay particles, according to an embodiment of the invention.

FIG. 3 shows the reflectance spectra of the colored clay particles, according to an embodiment of the invention.

FIG. 4 shows a composite bar graph of the change in the colorant strength of the coatings for the various colored Kaolin clays, according to an embodiment of the invention.

FIG. 5 is a composite of reflectance spectra over the in uv-visible spectral range from citrus leaves coated with colored clays, according to an embodiment of the invention.

FIG. 6A are photographs of colored clay coated citrus leaves according to an embodiment of the invention.

FIG. 6B shows a composite bar graph of the change in the colorant strength of citrus leaves for the difference of the leaves with and without coatings for the various colored Kaolin clays, according to an embodiment of the invention.

FIG. 7 shows a bar chart of selection of ACP for citrus trees coated with different colored clays, according to an embodiment of the invention, pigment-free clays, and bare leaves.

FIG. 8 shows photographic images of citrus plants coated with clay, dyed-clay, dyed clay+polymer adjuvant, dyed clay+Kollicoat and dyed clay+Xanthan Gum before and after exposure to 1-2, 4-5 and 7 cm of rainfall.

FIG. 9 shows a bar graph of mean photosynthesis for uncoated and colored clay coated citrus leaves, according to an embodiment of the invention, under green house conditions.

DETAILED DISCLOSURE

In an embodiment of the invention, colored kaolin clays are prepared that can be applied to alter the spectral reflectance of developing citrus leaves, thereby altering the optical cues that Asian Citrus Psyllid (ACP) use to identify citrus as a food source. The clays act as physical deterrent to *D. Citri* feeding and oviposition on the citrus leaves, including fresh flush, as the altered surface decreases ACP mobility and oviposition, and acts as a physical barrier to feeding. The colored clay particles result from surface modification of clays using surfactants and polymers, in a manner taught in Sharma et al WO/2013/123176, incorporated herein by reference. Kaolin clay particles present a negative charge on their surface while the edges have a positive charge. By appropriate selection of surfactant and polymers, the surface charge can be manipulated to present a desirable charge for adsorbing dyes, as shown in FIG. 1, where the dye is non-covalently attached to the surface of the clay particles.

These colored clay particles have the potential for use in application in crop protection, particle processing, paper, paints, and cosmetics. In the crop protection industry, color of the foliage plays an important role in the attack of the insect. As will be detailed below, colored clays can affectively change the reflectance of the foliage and help in camouflaging the foliage and thus prevent the attack of insect on crops. Additionally, some insects are attracted to some colors, and these colored clay coatings can be used to attract the insect to traps or non-crop areas for control. The colored clay particles can be used as tracers in particle processing where the colored clays are mixed with other materials and used for tracking particles through various flow based processes and determine mixing of materials. Kaolin is employed extensively in paper and paint industries and these colored clays can be substituted for uncolored kaolin in these applications. Cosmetics employ clay particles for a variety of applications and the colored clays disclosed herein can be used as excipients in cosmetics.

Particle film technology using clays has been reported to be an environment friendly, sustainable, and viable alternative to chemical insecticide for managing pests and diseases in agricultural crops (Glenn et al. *Horticultural Reviews* 2005, 31, 1-44). Kaolin clays have also been shown to be effective in reducing *Diaphorina citri* feeding on citrus leaves by inhibiting normal behavior (Hall et al.). Reflective colored kaolin clays on citrus plants to deter Asian Citrus Psyllid (*Diaphorina citri* Kuwayama)(ACP), the vector for *Candidatus liberibacter asiaticus*, were formed using a Surround® product (NovaSource International, Tessenderlo Kerley, Inc.) which are primarily calcined Kaolin clays. "Surround" Kaolin clays are EPA approved for insecticides and currently used for citrus crop protection from ACP. The clays act as a physical deterrent to *D. Citri* feeding and oviposition on the citrus leaves, including fresh flush. The altered surface decreases ACP mobility and oviposition, and acts as a physical barrier to feeding.

Figure 2:
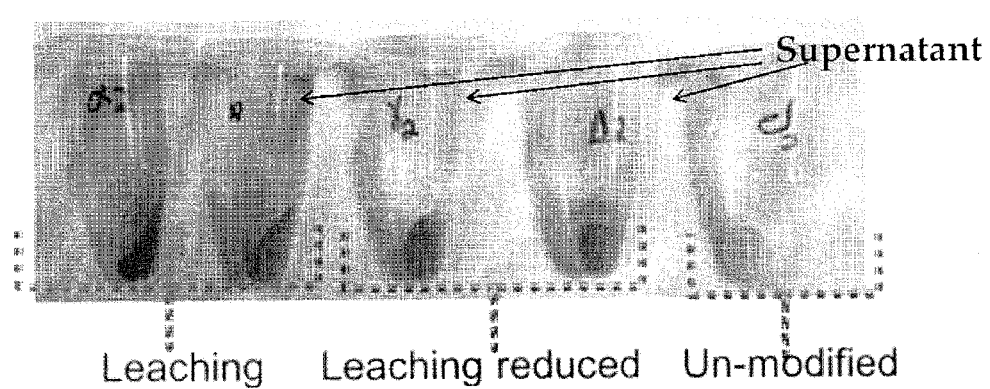

Dyes, including FDA certified colorants, absorbed on the clay particles are those approved for agricultural use by the EPA (list §180.920), covering a range of visible spectra for coating clays. Basic dyes are use for the colored clays according to embodiments of the invention. Surface modifications of the clay are required for doping with these dyes. Surface modifications are performed for kaolin clay products from different suppliers. Some of the clays change the optical reflectance of the absorbed dyes and others leached out earthly material during modification treatments which interfered with the doping process. Clay particles, that are originally white in appearance (devoid of any coloring contamination), are useful for adsorbing dyes and changing reflectance and are used for the particles, according to embodiments of the invention. Clay that retained the dyes reflectance property and remained suspended in solution (making it easier for spraying) are used. Many dyes successfully absorb to kaolin clays. A non-exhaustive list of dyes that can be used is FD&C Blue 2, FD&C Red 40, Basic Blue 54, Crystal Violet, and Basic Yellow 29, and D&C Violet 2. To prevent leaching of the dyes from the clay particles, according to an embodiment of the invention, optimal ratios of surfactant/polymer and dyes can be determined by systematic variation of the reagents. FIG. 2 shows the decrease in the leaching of the dye from the clays with increasing concentration of the surfactant. Treating clays with optimal concentration of the surfactants/polymers significantly reduces the leaching of dyes in solution.

Kaolin particles with different reflective properties that alter the wavelengths of light reflected by citrus foliage are prepared, according to an embodiment of the invention, and these particles lead to the obfuscation of the visible cues for ACP feeding. The kaolin clays are modified to increase adherence to the citrus foliage making them last longer during the rainy season. A plurality of applications are required to adequately coat a leaf surface with colored kaolin to alter preferred portions of light reflected from foliage, according to an embodiment of the invention.

Figure 3:
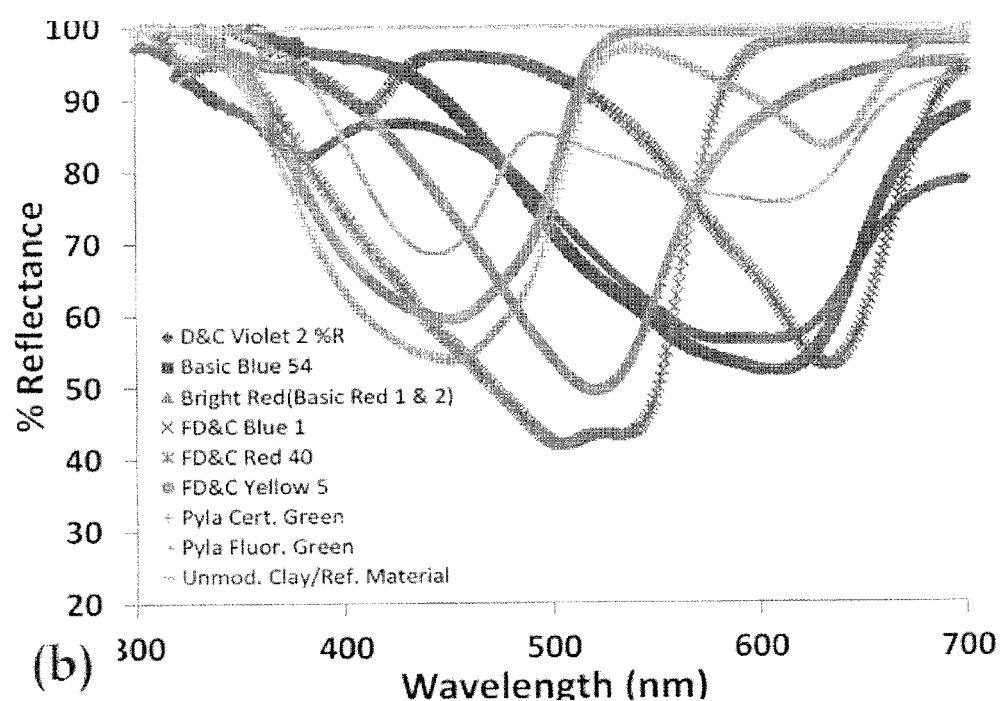

The synthesis methods, according to embodiments of the invention, have yielded different colored kaolin clay materials. To characterize the reflectance property of the colored clay particles, reflectance measurements were made on films of the clays on glass slides using an integration sphere set up. FIG. 3B shows reflectance spectra of films of clay coatings on glass slides where different dyes were employed to provide the color. Reflectance measurements were taken using a Lambda 800 UV/VIS Spectrometer. This instrument uses a standard reference material in combination with the sample, to measure how the percent reflectance differs in comparison to the reflectance of unmodified kaolin. Measurements of all modified clay materials were taken with respect to unmodified Surround® WP Kaolin Clay between the wavelengths of 300 to 900 nm. Each colored material displays reflectance within the Visible to Near Inferred range, as shown in FIG. 3. For example, kaolin modified with FD&C Red 40 dye has altered reflectance between 375-575 nm, kaolin modified with D&C Violet 2 has altered reflectance between 475-600 nm, and kaolin modified with a fluorescein dye has an altered reflectance between 575-650 nm and 425-475 nm. Some of the dyes, e.g., FD&C Violet −2 and FD&C Red 40 additionally change reflectance in the UV region (below 400 nm).

In addition to reflectance and color index measurements, zeta potential determinations were determined using a ZetaPlus, Zeta Potential Analyzer from Brookhaven Instruments. Surface charge of the starting material changes after applying the dye modifications to the material. Unmodified kaolin clay shows a Zeta Potential of about −31 mV. The acidic dye modified clay materials show a significant increase of zeta potential that ranges from a Zeta Potential of +5 to +22 mV at pH 6.5. Kaolin modified with basic dyes display Zeta Potentials that vary between −13 to −23 mV.

Figure 4:
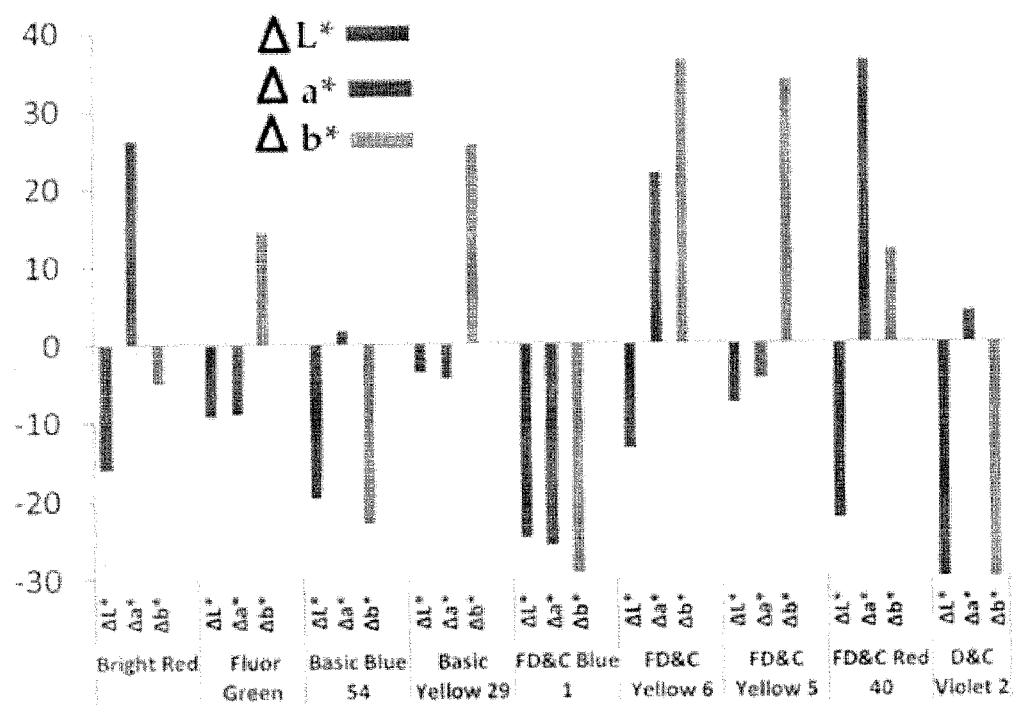

In another embodiment of the invention, the clays change the visual appearance of substrates, as was determined for exemplary samples by measuring the color index of the leaves using MiniScan XE Plus Spectrophotometer (Hunter Labs). The CIE L*a*b* color scale (Korifi et al. *Talanta* 2013, 104, 58-66, Becerir *Tekst Konfeksiyon* 2010, 20(2), 145-54) as derived from the XYZ color space is used in measuring the color of the particles developed. The L* scale describes luminance where L*=0 is black and L*=100 is diffuse white. Positive a* is red and negative a* is green. Positive b* is yellow and negative b* is blue. Colorant strength is defined as a pigment or dye's ability to change the color of an otherwise colorless material. FIG. 4 shows the change in the colorant strength of these coatings with respect to "Surround" kaolin clays. As can be seen from FIG. 4, Bright red and FD&C Red 40 coatings produce a significant enhancement in red scale while Basic Blue, FD&C Blue 1 and FD&C violet 2 cause an enhancement in the blue.

Trees with Hamlin orange scions grafted to Swingle rootstock were obtained from a commercial citrus nursery and grown in a greenhouse with a 14/10 light dark cycle of supplemental illumination. Plants were irrigated daily and treated with a slow release fertilizer every three months. Trees were allowed to acclimate to the new greenhouse for three months. During this time all trees produced a new flush of leaves. Six fully expanded leaves were selected at random from the total population of leaves and sprayed with one of the colored kaolin suspensions. The first application was allowed to completely dry before a second application was applied to the leaf; which was held overnight for complete drying. Leaves from the plants were used for performing the gas exchange and reflectance studies.

Figure 5:
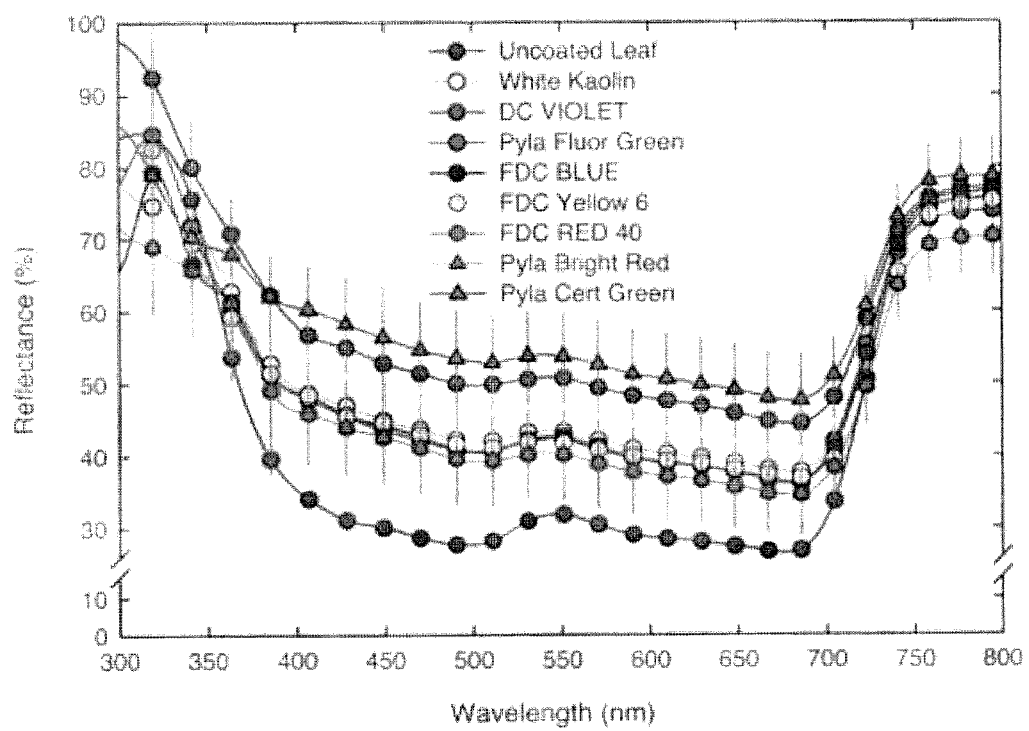

Leaves were excised from the parent plants with a razor blade and brought to the lab in plastic bags while taking extreme care not to disrupt the Kaolin coating. A 2 cm diameter circular leaf punch was excised from the leaf with a cork borer and mounted to the port of a 10 cm diameter integrating sphere located 90° along the sphere's equator from the light entry port and 180° from the fiber optic cable sensor port. Six leaves from each Kaolin solution treatment were mounted individually onto the sample port and reflectance values from 300-800 nm were recorded using a fiber coupled Ocean Optics spectrometer. These values were used to calculate a mean and standard deviation for each treatment across the 300-800 nm range. FIG. 5 shows the reflectance spectra obtained with the colored kaolin clays on Hamlin orange citrus leaves.

Uncoated leaves generally had the lowest reflectance values across the visible range of photosynthetically active wavelengths (400-700 nm). In the ultraviolet (300-350 nm) range, the FD&C Violet Kaolin suspension had the highest reflectance values (94%) and the Bright Red Kaolin solution had the lowest (68%). Most Kaolin suspensions had very similar reflectance values to the white, commercial Kaolin solution across the 350-750 nm range. The DC Violet and Cert Green Kaolin solutions had higher reflectance values across the 400-700 nm range. Overall, the majority of the Kaolin suspensions flattened the reflectance curve relative to uncoated leaves by increasing reflectance in the 400-500 nm range. There was little change to the shape of the reflectance curve above 550 urn other than increasing the total reflectance by approximately 15-20% for most Kaolin suspensions, and up to 30-35% for the FD&C Violet and Pyla Cert Green.

Figure 6A:
Figure 6A:
Figure 6B:
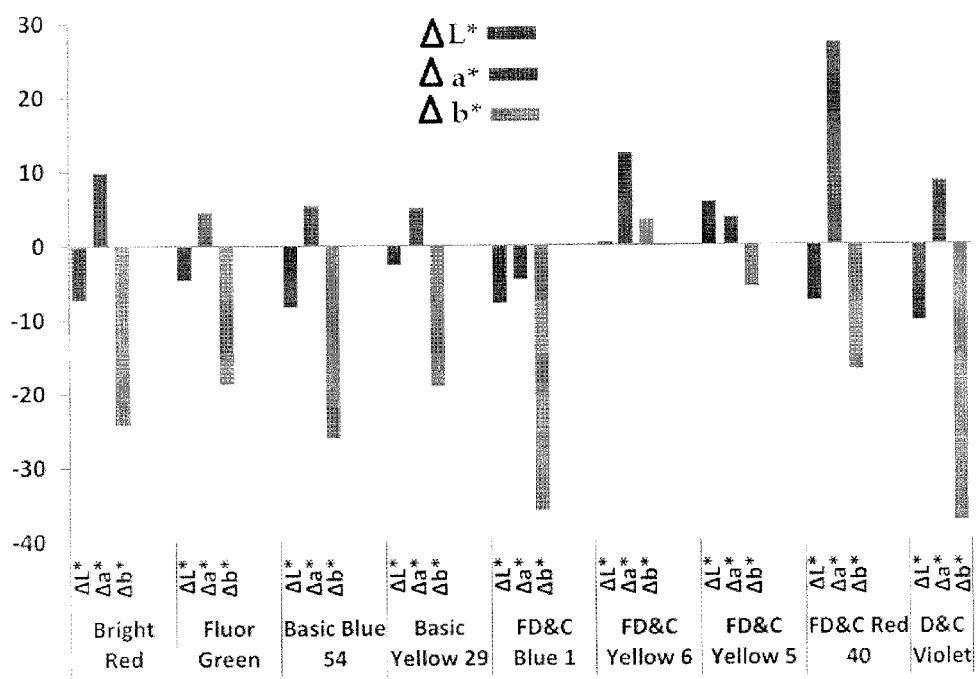

In addition to reflectance measurements, the colorant strength measurements were also made on citrus leaves (Valentia orange) coated with colored clays. FIG. 6A shows the representative images of the colored clay coating on the foliage as well as the change in the colorant strength upon coating with colored clays (FIG. 6B). The ability of these clays to change the visual appearance of the foliage is determined by measuring the color index of the leaves using MiniScan XE Plus-Spectrophotometer (Hunter Labs). The citrus leaves were coated with clays at concentrations of 0.45 and 0.11 g clay per mL water and the color index was measured after drying of coatings. Trends similar to those obtained with glass slides as substrate are observed. The values determined are not absolute values and will change with the amount, adhesion, and coverage of coating as well as reflectance of the citrus leaves. Thick coatings are effective in significantly altering the colorant strength of the leaves, for example, FD&C Red 40 and Bright red increase the red scale while FD&C Blue 40 and FD&C violet significantly increase the blue strength.

Figure 7:
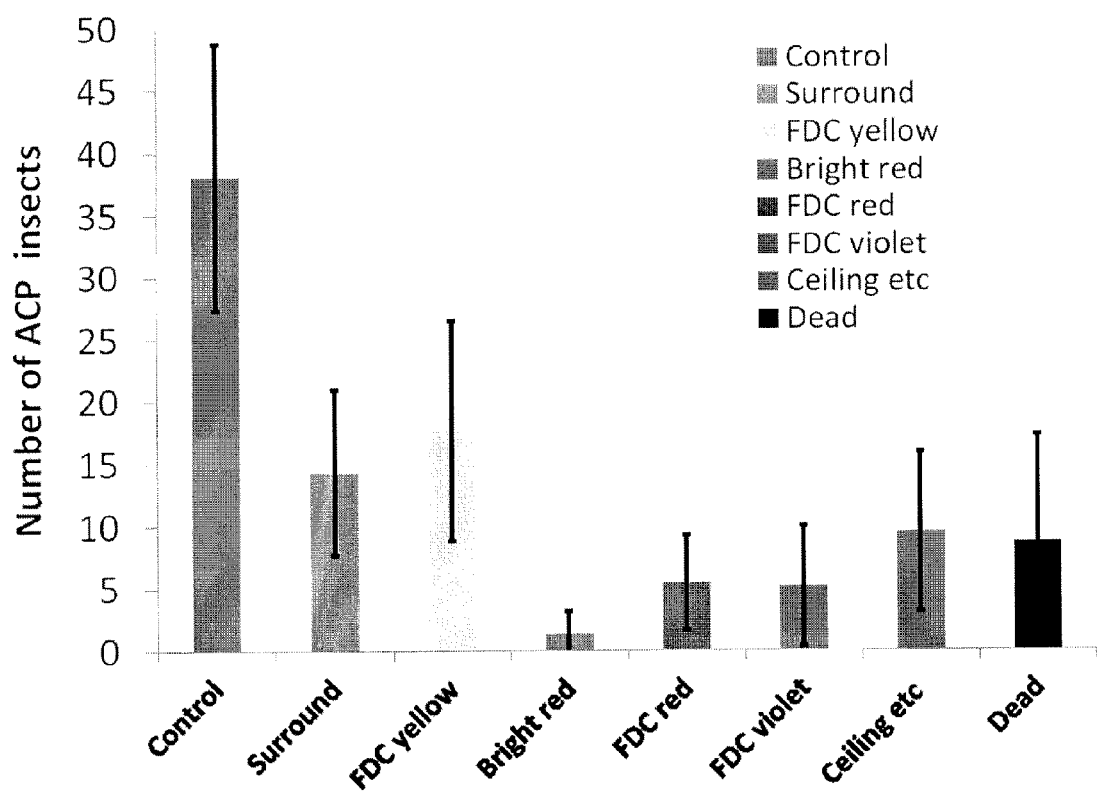

Four colored clay materials developed to cover the visible spectrum were selected to be applied on citrus plants and ACP inhibition tests. Clay suspensions of about 160 g/L were employed for ACP tests using clays with the dyes FD&C VIOLET 2, FD&C YELLOW 5, FD&C RED 40 and PYLM Bright Red. The colored clays and control (white surround clay) were applied to the leaves of citrus plants to deter the Asian citrus Psyllid *Diaphorina citri* from citrus crops and, therefore, prevent the spread of Citrus Greening disease. The experiment was performed 5 times on different days. Four cages were set up, each having six plants that were arranged randomly. The cages included: Control (no treatment); Surround-clay; Bright Red-clay; FDC Yellow-clay; FDC Violet-clay; and FDC Red-clay. One hundred psyllids were released in the cage (choice experiment) and given 24 hours to choose a location before counts were made. The controls used were uncoated tree and "Surround" clay coated tree. FIG. 7 shows the results from the treatment and the values are the number of psyllids on each tree. ACP has very low preference for Bright red, followed by FDC Red and FDC Violet colored trees. FDC Yellow clays attract more than surround coated (white) trees. The color can be applied in conjunction with the other colors to deviate the insect to a trap comprising leaf coated with FDC Yellow. Clay coatings with Bright red, FDC Red and FDC Violet clay coatings increase the red and the blue colors significantly from the green color of the foliage, as shown in FIG. 6B. The Bright red coatings, as shown in FIG. 5, presented lowest reflectance values in the UV region. The bright red pigment had about 10-15% lower reflectance in the UV compared to uncoated leaves. A combination of UV and visible reflectance influences ACP selection of citrus foliage for feeding.

Preliminary experiments were conducted to determine the efficiency of dye-doped kaolin clay formulations to increase rain fastness. Several formulations were prepared with different adjuvants to determine how well clay particles adhere to citrus foliage. Adjuvants were selected based on their ability to act as stickers, binders and viscosity modifiers. Formulations were sprayed on orange trees at a concentration of 0.4 lbs. per gallon and a total, spraying of 0.96 grams on eight to ten mature leaves was achieved.

Formulations with agricultural grade adjuvants, spreaders, stickers, and colored clay (FD&C Yellow 6) were prepared. Some of the adjuvants tested for the rain fastness experiments include: Lutrol F87 surfactant; Lutrol F108 surfactant; Lutrol F127; Pluronic L64; Pluronic L81; Induce; Xanthan Gum; Guar Gum; Kollicoat (30% poly vinyl acetate dispersion in water); 1% poly vinyl alcohol (Mw 13K-20K); Polymer adjuvant (6% sodium poly acrylate in water); Diamond Cling (pinene polymer, nonionic surfactant, formulation acids, and polydimethylsiloxane); Triton X-100; and 1% Cohere (nonionic surfactant, alkanolamide surfactants, and alkylarylpolyethoxyethanol sulfates at 90% in water).

Mixing of some of the adjuvants with dye doped kaolin clays resulted in color loss due to leaching of the dyes. Formulations that resulted in dye replacement included those with: Diamond Cling; Triton X-100; Pluronic L64; Pluronic L81; Induce; Lutrol F127; and Cohere. These adjuvants appear to competitively adsorb on the clay particles, leading to desorption of the dye from the clay particles. The formulations that did not interfere with the colored kaolin clays were sprayed on live citrus foliage in the manner described above. Images of the initial coatings were taken after drying. The coated leaves were sprayed evenly with 100 mL of water using a sprayer and evaluated post drying. Formulations that resulted in relatively uniform coatings and withstood the water spraying were Kollicoat, Polymer adjuvant and Xanthan Gum. The formulations that passed these initial screening were tested under rainfall.

Figure 8:
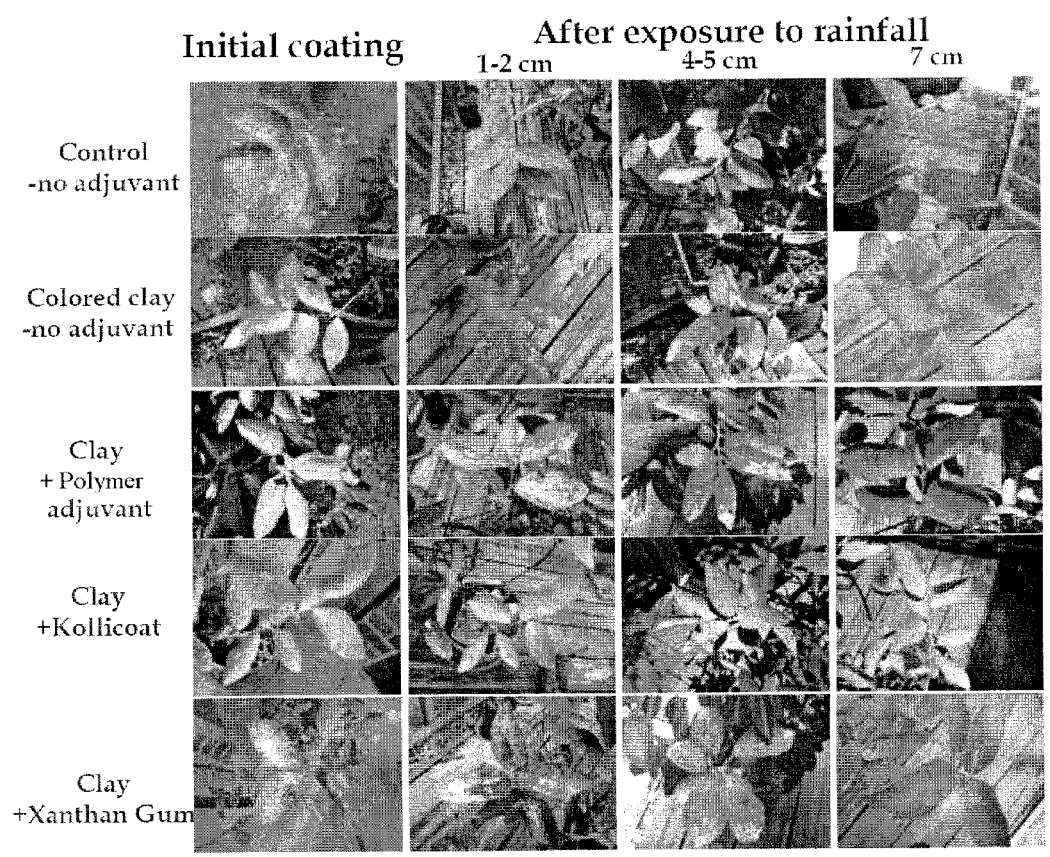

Several formulations containing different concentration of Kollicoat, Polymer adjuvant and Xanthan Gum were sprayed on to citrus plants. Controls of dyed and white kaolin clay without the addition of any adjuvants were also coated on leaves for rain fastness test. After drying overnight, the coatings remained on the citrus foliage for several days. The coatings were evaluated after 1-2, 4-5 and 7 cm of rainfall. FIG. 8 shows images of citrus plants coated with clay, dyed-clay, dyed clay+polymer adjuvant, dyed clay+ Kollicoat and dyed clay+Xanthan Gum before and after exposure to 1-2, 4-5 and 7 cm rainfall. From visual examination of the images Polymer adjuvant and Kollicoat were determined to be the best adjuvants for improving spreading and rain fastness of kaolin clay, withstanding up to 7 cm rain. Kollicoat, a pharmaceutical excipient, is primarily poly vinyl acetate dispersed in water and stabilized with povidone and sodium dodecyl sulfate, which acts a polymeric binder and helps in the better adhesion of the clay particles to the leaves. In addition kaolin coatings are formed as thin films as compared to other adjuvants. Polymer adjuvant comprising sodium poly acrylate in water performed next best withstanding up to 4-5 cm rainfall. It was noted that the addition of the polymer to the clay formulations resulted in an increase of mean particle size by 5-10 µm, indicating a tendency of the clay particles to aggregate in the presence of the adjuvant, resulting in thick coatings.

Figure 9:
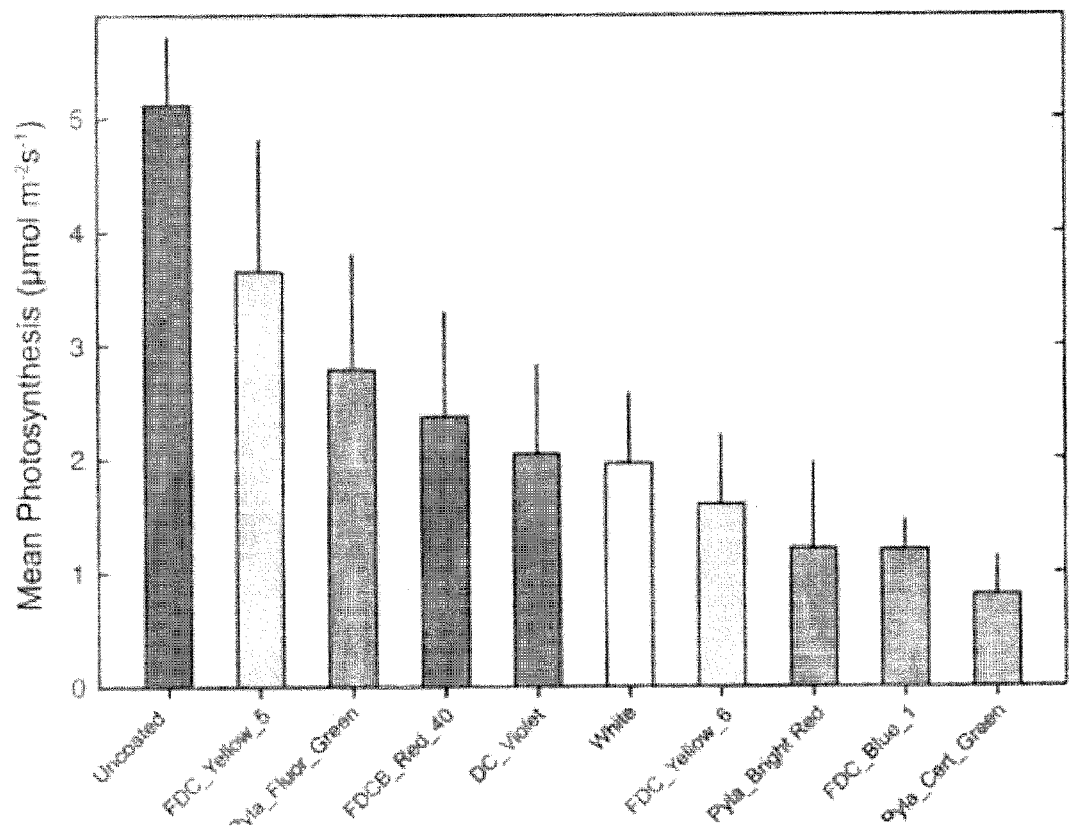

Trees with Hamlin orange scions grafted to Swingle rootstock were grown in a greenhouse with a 14/10 light dark cycle of supplemental illumination. Plants were irrigated daily and treated with a slow release fertilizer every three months. Trees were allowed to acclimate to the new greenhouse for three months before the experiments began. During this time all trees produced a new flush of leaves. Six fully expanded leaves were selected at random and sprayed with two coatings of the kaolin suspensions. After overnight drying, the following day, each leaf was mounted in the chamber of a Li-6400 gas exchange system with the LED light source providing 1000 $\mu molm^{-2}s^{-1}$ Photosynthetic Photon Flux Density. Relative humidity in the chamber was regulated to be within 5% of the ambient conditions in the greenhouse. The $CO_2$ level in the chamber was set at 400 ppm. The photosynthetic rate was monitored for approximately 15 minutes for each leaf as the values stabilized, at which point the gas exchange data was continuously logged at ten second intervals for five minutes. The data were used to calculate a mean instantaneous photosynthesis value for each leaf averaged over the five minute observation period. Mean values and standard deviations were calculated for leaves coated with each kaolin solution with an ANOVA with post-hoc Bonferonni correction in SPSS to test for statistical significance. FIG. 9 shows gas exchange data for double coated leaves with each of the different pigments.

Photosynthetic rates were highest in uncoated leaves, and every Kaolin solution treatment resulted in significantly ($p<0.05$) lower values. There was no apparent relationship between the pigment colors and photosynthesis, but some Kaolin solutions did adhere better than others.

There was some variability in all of the treatments, but the variability was relatively consistent between treatments, and was likely due to the variability of applying the Kaolin suspension. Single applications of the Kaolin suspensions were highly variable, and a second coating reduced the variability in the visual appearance of the surface coating. The white, commercial Kaolin suspension, Surround®, reduced the mean photosynthetic rate by approximately two fold compared to uncoated leaves. Four colored Kaolin coatings showed higher mean photosynthetic values and four lower as compared to white clay. Some of this variability is consistent with the degree to which the coatings adhered to the leaf surface and the reflective properties of the Kaolin solutions.

The lowest photosynthetic values were observed in the Pyla Cert Green Kaolin solution, which also had the highest reflectance values over the photosynthetically active wavelengths (400-700 nm). Reflectance values for the other pigments with lower photosynthetic rates were nearly indistinguishable from the commercial Kaolin solution. In general, reflectance in the blue wavelengths that are important for photosynthesis was significantly higher in all of the Kaolin solutions. Field grown trees with white Kaolin solution applications can have higher photosynthetic rates relative to uncoated leaves (Jifon et al. *Journal of the American Society for Horticultural Science* 2003, 128(1), 107-12), as the light environment in field conditions is significantly different where field grown trees are often light saturated. Decreasing the total radiation load on leaves in field grown conditions is likely responsible for the reported increases in photosynthesis. In these greenhouse studies, the leaves were not light saturated and, therefore, a decrease in the total radiation load leads to light limitations to photosynthesis.

All patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. Colored clay particles, comprising a kaolin clay particle with one or more absorbed pigments and a cationic surfactant, wherein the colored clay particles display increased reflectance of red and blue colors wherein the absorbed pigment is PYLM Bright Red, FD&C Red 40, or FD&C Violet 2, and optionally increased reflectance of near ultraviolet light.

2. The colored clay particles according to claim 1, wherein the surfactant is cetylpyridinium chloride.

3. The colored clay particles according to claim 1, further comprising an adjuvant for spreading and sticking.

4. The colored clay particles according to claim 3, where the adjuvant is Xanthan Gum; poly vinyl acetate dispersion in watery; or sodium poly acrylate in water.

5. A method of repelling insects from a surface, comprising:
   providing a multiplicity of colored clay particles according to claim 1; and
   coating the colored clay particles on a surface.

6. The method of claim 5, wherein coating is spraying a suspension of the colored clay particles.

7. The method of claim 5, wherein the surface is a surface of a plant.

8. The method of claim 5, wherein the plant is a citrus plant.

9. The method of claim 5, further comprising a trap surface.

10. The method of claim 9, wherein the trap surface is a surface of a plant having a multiplicity of colored clay particles comprising FD&C Yellow.

* * * * *